United States Patent [19]

Stavropoulos et al.

[11] 4,142,517
[45] Mar. 6, 1979

[54] APPARATUS FOR EXTRACTING BONE MARROW SPECIMENS

[76] Inventors: Stamatios M. Stavropoulos, 2277 Live Oak Dr. W., Los Angeles, Calif. 90068; Elvia E. Contreras Guerrero de Stavropoulos, AP 80249, Caracas 108, Venezuela

[21] Appl. No.: 708,162

[22] Filed: Jul. 23, 1976

[51] Int. Cl.² ............................................. A61B 10/00
[52] U.S. Cl. ..................................... 128/2 B; 128/310
[58] Field of Search ................ 128/2 B, 2 R, 310, 347

[56] References Cited

U.S. PATENT DOCUMENTS

| 1,213,001 | 1/1917 | Philips | 128/347 |
|---|---|---|---|
| 2,496,111 | 1/1950 | Turkel | 128/2 B |
| 2,516,492 | 7/1950 | Turkel | 128/2 B |
| 3,404,677 | 10/1968 | Springer | 128/2 B |
| 3,587,560 | 6/1971 | Glassman | 128/2 B |
| 4,010,737 | 3/1977 | Vilaghy et al. | 128/2 B |

FOREIGN PATENT DOCUMENTS

| 496458 | 10/1950 | Belgium | 128/347 |
|---|---|---|---|
| 459483 | 5/1928 | Fed. Rep. of Germany | 128/347 |
| 949943 | 9/1949 | France | 128/347 |

*Primary Examiner*—Kyle L. Howell
*Attorney, Agent, or Firm*—Huebner & Worrel

[57] ABSTRACT

The device is comprised of a guide tube having an inner end cutting edge and during insertion, carries a stylet to prevent the collection of blood and skin tissue. Adjustable guard means are on the tube for predetermining and limiting the depth of entry. After the tube has been inserted to the proper depth, the stylet is removed and a hollow needle is inserted through the tube and the bone structure into the marrow cavity to obtain a marrow sample. There are means on the needle to provide for the predetermined and limited depth of entry of the needle and motor means are provided to rotate the needle to cut through the bone and enter the marrow cavity to obtain a marrow sample. In addition after the needle has been removed, the guide tube is adapted to penetrate the bone and be moved into the marrow cavity, at which time aspiration means are connected to the outer end of the tube to aspirate marrow into the aspiration means.

5 Claims, 6 Drawing Figures

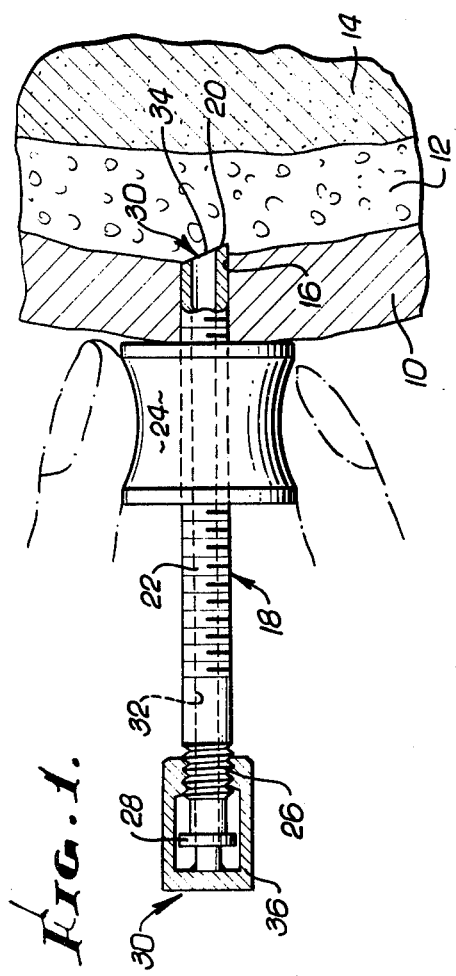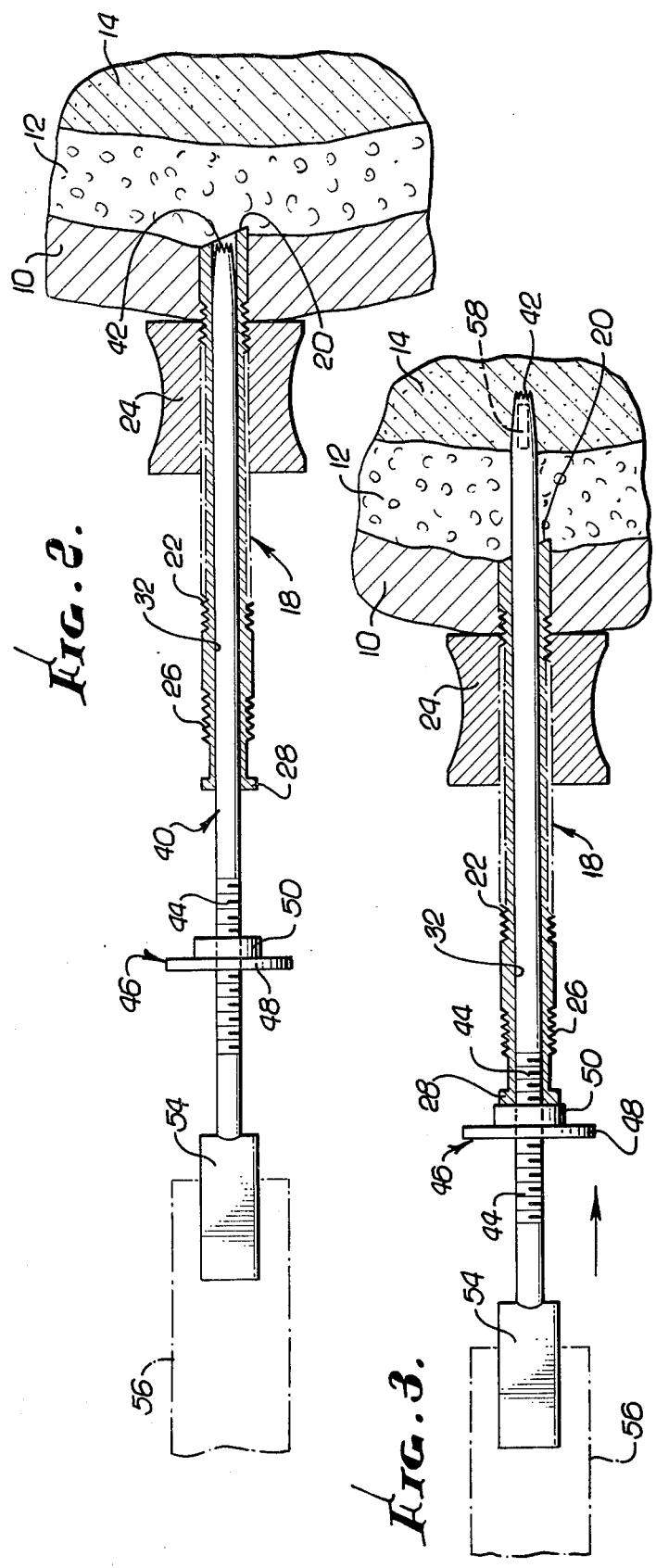

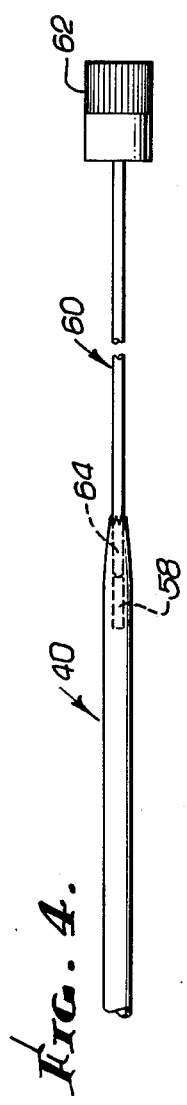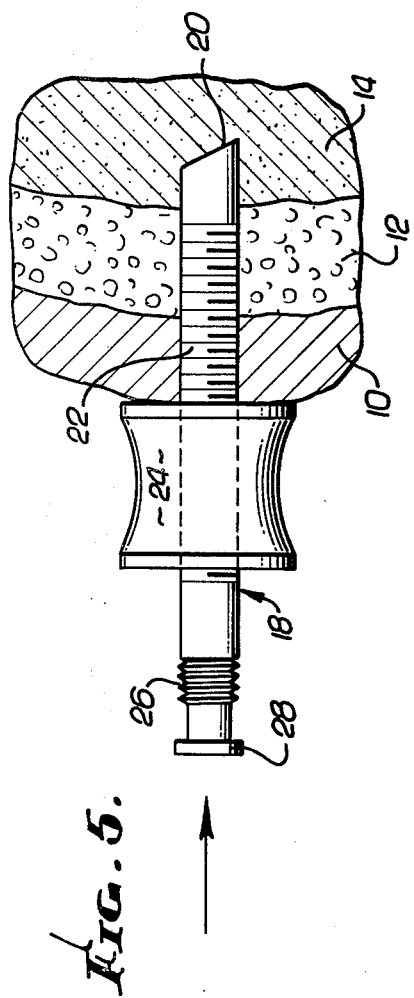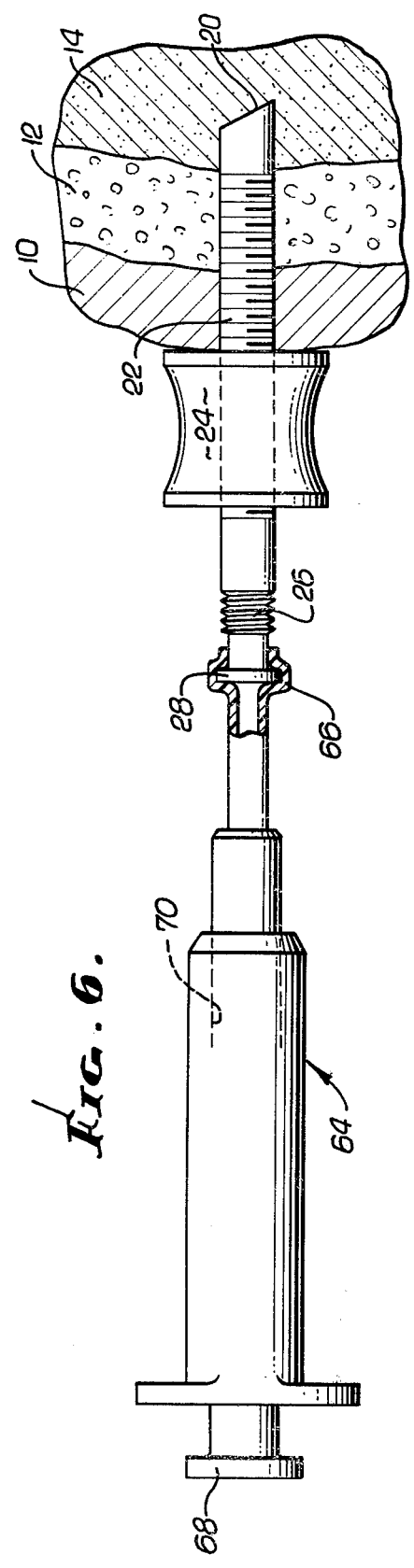

APPARATUS FOR EXTRACTING BONE MARROW SPECIMENS

BACKGROUND OF THE INVENTION

The invention relates to extracting solid samples of marrow from a bone marrow cavity and the aspiration of fluid marrow without removing the device from the incision.

In the prior art, biopsy needles have had the disadvantages of collecting skin tissue and blood mixed with marrow specimens so as to prevent the obtaining of good samples. With these needles it is difficult, even with repeated attempts, to obtain adequate specimens, particularly from patients with myelofibrosis and depleted, fatty bone marrows.

Aspirated bone marrow taken with the prior art needles is typically not truly representative of the marrow as it tends to be composed of a mixture of particles of the marrow and peripheral blood. In these situations the gross appearance and the total nucleated cell count of the aspirated fluid do not furnish reliable estimates of the cellularity. It has been found that these types of samples from the same marrow source have wide variations in the total counts of nucleated cells. This has resulted in conflicting descriptions of normal and abnormal marrows. To overcome these problems in the prior art, the additional steps of mixing the aspirate with an anticoagulant and centrifuging the mixture, and examining the sediment have been used. Another method is to make smears and imprints of particles of solid marrow selected from the aspirate.

The failure to obtain good samples has required performance of multiple aspirations and in some cases surgical trephine for biopsy has had to be undertaken where repeated aspirators have failed to yield marrow cells or particles of diagnostic value.

SUMMARY OF THE INVENTION

With the present device, samples of marrow are successfully taken without being diluted with blood, and the samples are not distorted or compressed. The ability to obtain undistorted specimens tends to eliminate the bias in the interpretation of the marrow structure and cellularity.

Accordingly, it is an object of the invention to provide an improved apparatus for extracting bone marrow specimens.

It is another object of the invention to provide a device, as described in the preceding paragraph, that is simple in structure and operation and well-tolerated by the patient.

It is a further object of the invention to provide an apparatus, as described in the preceding paragraphs, in which biopsy and aspiration can be accomplished with one incision and one insertion of a single tube through which both the biopsy (solid sample, i.e. bone and marrow tissue) and the aspiration (cellular tissue) are accomplished in a single operation.

It is another object of the invention in which the apparatus, as described in the preceding paragraphs, avoids skin tissue and allows only a minimum of blood in the specimens.

It is still another object of the invention to provide an apparatus, as described in the preceding paragraphs, in which bone tissue and a solid marrow specimen even though intermixed can be easily removed from the needle due to its configuration.

Further objects and advantages of the invention may be brought out in the following part of the specification wherein small details have been described for the competence of disclosure, without intending to limit the scope of the invention which is set forth in the appended claims.

BRIEF DESCRIPTION OF THE DRAWINGS

FIG. 1 is a partially cross-sectional view of a guide tube and depth guard, a stylet being in the tube according to the invention;

FIG. 2 is an elevational view of a biopsy needle in the guide tube in position to be moved through the bone and into the marrow cavity;

FIG. 3 is a view of the structure shown in FIG. 2, illustrating the collection of the marrow sample by the biopsy needle in the marrow cavity;

FIG. 4 is a fragmentary view illustrating the means for removal of a marrow specimen from the biopsy needle;

FIG. 5 is a view illustrating the positioning of the guide tube into the marrow cavity after the biopsy needle has been removed; and FIG. 6 is a view of the guide tube connected to an aspirator for aspirating bone marrow from the marrow cavity.

DESCRIPTION OF THE PREFERRED EMBODIMENTS

Referring again to the drawings, in FIGS. 1-3 there is shown a fragmentary view of skin tissue 10, cortical bone 12, and marrow cavity 14. A small incision 16 has been made through the skin to the bone and inserted therein is a guide tube 18 having an inner or forward beveled cutting edge 20 slightly penetrating the bone 12 to aid in holding it in place. The tube has external threads 22 with which a spool-shaped, depth indicating and limiting guard 24 is threadedly engaged, the guard 24 being adjustable on the guide. The guard can be generally positioned before insertion of the tube after physical inspection of the thickness of the skin. The outer spool surface is gripped as shown for insertion and after insertion, if it is not in abutment with the skin, it is rotated so as to abut.

Adjacent the outer end of the tube are external threads 26, and spaced rearwardly or outwardly therefrom is an annular flange 28 on the end of the tube. The tube has an internal cylindrical passage 32 extending therethrough.

Slidably and snugly engaged within the passage 32 is a stylet, generally designated as 30. The stylet has a beveled inner end 34 which fits flush with the cutting edge 20 so as to prevent the entry of any material into the passage while the stylet is in place. The outer end of the stylet has a cap 36 having internal threads engaged with the threads 26 on the tube to securely position the inner end 34 to be flush with the cutting edge 20.

In FIG. 2 the stylet 30 has been removed and in its place is a biopsy needle, generally designated as 40, slidably engaged within the tube passage. The needle is hollow and has a serrated cutting edge 42 on its inner end. Outwardly of the flange 28 the needle has external threads 44 threadedly engaged with a depth limiting or measuring guard 46 formed of integral disks 48 and 50. Needles can be of various diameters and lengths for use with a particular guide tube. Secured to the outer end of the needle is a drill chuck 54 fitted within an electric drilling motor 56 for driving the needle through the bone.

In FIG. 3 the needle has been rotated by the motor so that its inner end has penetrated the bone and entered the marrow cavity so as to have obtained therein a biopsy specimen 58. The depth of penetration of the needle into the marrow cavity has been limited by the abutment of the depth limiting guard 46 with the flange 28 on the outer end of the tube. While bone wall thicknesses and marrow cavity diameters are not exactly known, the expertise of the physician of anatomy will allow the guard 46 to be selectively adjusted and positioned to permit the needle to move a selected predetermined distance into the marrow cavity.

In FIG. 4 the needle having the sample 58 has been withdrawn from the tube. A stylet 60 having an outer end knob 62 and an inner end 64 extends into the inner end of the needle for the purpose of extruding the biopsy specimen from the outer end of the needle. The sample 58 is comprised of the combination of solid marrow and bone, but does not include any skin tissue and has very little blood mixed therewith.

After the needle has been withdrawn, the guide tube 18 is slightly penetrating the bone 12 and is in position to be inserted to accomplish aspiration of marrow in a fluid state. While the marrow is still a solid substance when aspiration is accomplished, the sample is mixed with some peripheral blood and can be referred to as "fluid marrow" for the sake of illustration. The guard 24 is rotated before insertion on the threads 22 to a more outwardly position to permit the proper depth penetration of the inner end of the tube. The proper depth is known, depending upon the age of the patient. After this depth has been measured on the tube, the guard 24 is then properly positioned and the tube is forced through the bone, which is easily penetrated by the cutting edge 20, aided by the prior insertion of the needle. If it is necessary or desirable, this penetration can be made with the stylet in place, as shown in FIG. 1.

As shown in FIGS. 5 and 6, after the penetration of the tube into the marrow has been accomplished, the stylet, if used, is removed and an aspirator or syringe, generally designated as 64, having an internal cylindrical surface 70 in which plunger 68 is sealingly and slidably engaged. The syringe is attached to the flange 28 of the tube by means of a tubular elastic-lipped outer end member 66 into which the flange 28 is easily and tightly snap-fitted. To aspirate the "fluid marrow" the plunger 68 is partially withdrawn from the cylinder 70, the plunger withdrawal causing a suction to fill the syringe with the "fluid marrow."

The biopsy with the present invention yields an ample, undistorted sample and, similarly, the aspiration produces the extraction of relatively pure fluid marrow, substantially free of undesirable other material. During the respective operations the guards 24 and 46 prevent excessive penetration into the bone and marrow cavity.

The invention and its attendant advantages will be understood from the foregoing description and it will be apparent that various changes may be made in the form, construction and arragement of the parts of the invention without departing from the spirit and scope thereof or sacrificing its material advantages, the arrangements hereinbefore described being merely by way of example. We do not wish to be restricted to the specific forms shown or uses mentioned except as defined in the accompanying claims, wherein various portions have been separated for clarity of reading and not for emphasis.

We claim:

1. A device for extracting marrow from a bone, comprising:
    a tubular guide having an inner and outer end,
    external threads on said guide adjacent said inner end,
    said guide having a cutting edge on its inner end adapted to cut through the skin and to penetrate the bone surface and to aid in holding the guide in place in the bone,
    a guide depth guard having internal threads engaged with said external threads adjacent said inner end, said guide being adapted to indicate and limit the desired length of insertion of the guide to penetrate the bone,
    said depth guard being rotatable on said guide toward and away from said inner end and having means close to the skin to be gripped for insertion of the guide into the skin and bone,
    said depth guard being adapted to abut the skin and prevent additional penetration of the guide when the guide has been inserted to the selected depth,
    a hollow needle having a conical inner end having a cutting edge and an outer end engaged with rotation means for rotation thereby, said conical inner end having an axially directed opening in said inner end within said cutting edge to receive and retain marrow therein,
    said needle being slidably fitted within said guide with its inner end adjacent the inner end of said guide when said guide has penetrated the bone,
    said needle having its outer end extending outwardly of the outer end of the guide,
    said needle having external threads adjacent the outer end of the guide, portions of said threads being adapted to be positioned to extend simultaneously into the guide and outwardly of the guide, and
    a measuring guard threadedly engaged on said threads on said needle outwardly of said guide to limit inward movement of the needle in said guide and into the marrow of the bone, said threads on said needle being of substantial length to permit substantial longitudinal adjustment of the measuring guard on the needle to substantially vary the limit of said inward movement, said measuring guard limiting the inward movement by abutting the outer end of the guide.

2. The invention according to claim 1 in which:
    said means to be gripped on said depth guard is generally spool-shaped.

3. The invention according to claim 1 in which:
    said measuring guard is a disk.

4. The invention according to claim 1 including:
    a motor connected to said needle adjacent its outer end to rotate the needle through the bone and into the marrow.

5. The invention according to claim 1 in which:
    said guide has means on its outer end for connecting to an aspirator when said needle has been removed whereby a marrow sample can be withdrawn from the marrow cavity.

* * * * *

UNITED STATES PATENT AND TRADEMARK OFFICE
CERTIFICATE OF CORRECTION

PATENT NO. : 4,142,517

DATED : March 6, 1979

INVENTOR(S) : Elvia E. Contreras Guerrero De Stavropoulos et al.

It is certified that error appears in the above-identified patent and that said Letters Patent are hereby corrected as shown below:

On the title page, item [76] Inventors: should read

-- Elvia E. Contreras Guerrero de Stavropoulos, AP 80249, Caracas 108, Venezuela; Stamatios M. Stavropoulos, 2277 Live Oak Dr. W., Los Angeles, Calif. 90068 --.

Signed and Sealed this

Nineteenth Day of June 1979

[SEAL]

Attest:

RUTH C. MASON
*Attesting Officer*

DONALD W. BANNER
*Commissioner of Patents and Trademarks*